(12) United States Patent
Lunz et al.

(10) Patent No.: US 11,389,695 B2
(45) Date of Patent: Jul. 19, 2022

(54) BREATHING TRAINING, MONITORING AND/OR ASSISTANCE DEVICE

(71) Applicant: KONINKLIJKE PHILIPS N.V., Eindhoven (NL)

(72) Inventors: Manuela Lunz, Waalre (NL); Teunis Johannes Vink, Valkenswaard (NL); Leendert Van Der Tempel, Eindhoven (NL); Mareike Klee, Straelen (DE); Lenneke Van Genugten, Eindhoven (NL); Neil Francis Joye, Waalre (NL); Franciscus Hendrikus Van Heesch, Eindhoven (NL); Edwin Van Rutten, Eindhoven (NL); Jeroen Herman Lammers, Eindhoven (NL); Gabriele Spina, Eindhoven (NL); Albertus Cornelis Den Brinker, Eindhoven (NL); Kevin Paul Warmerdam, Eindhoven (NL); Sander Kruitwagen, Eindhoven (NL); Andrew Mitchell, Eindhoven (NL); Denny Mathew, Eindhoven (NL); Achim Gerhard Rolf Koerber, Eindhoven (NL); Frank Bies, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 174 days.

(21) Appl. No.: 15/771,099

(22) PCT Filed: Oct. 13, 2016

(86) PCT No.: PCT/EP2016/074596
§ 371 (c)(1),
(2) Date: Apr. 27, 2018

(87) PCT Pub. No.: WO2017/071964
PCT Pub. Date: May 4, 2017

(65) Prior Publication Data
US 2018/0318642 A1     Nov. 8, 2018

(30) Foreign Application Priority Data

Oct. 30, 2015  (EP) .................................... 15192426

(51) Int. Cl.
*A63B 21/02* (2006.01)
*A61M 16/12* (2006.01)
(Continued)

(52) U.S. Cl.
CPC ....... *A63B 23/185* (2013.01); *A61M 16/0066* (2013.01); *A61M 16/024* (2017.08);
(Continued)

(58) Field of Classification Search
CPC ............ A63B 71/0622; A63B 24/0087; A63B 21/0087; A63B 21/00069;
(Continued)

(56) References Cited

U.S. PATENT DOCUMENTS

| 3,729,678 A | 4/1973 | Glasbergen |
| 3,739,775 A | 6/1973 | Helm |
(Continued)

FOREIGN PATENT DOCUMENTS

| DE | 102007014465 A1 | 12/2007 |
| EP | 1568391 A1 | 8/2005 |
(Continued)

OTHER PUBLICATIONS

Metered-dose inhaler definition, American Academy of Allergy Asthma & Immunology (Year: 2020).*
(Continued)

*Primary Examiner* — Samchuan C Yao
*Assistant Examiner* — Nathan M Le
(74) *Attorney, Agent, or Firm* — Daniel H. Brean

(57) ABSTRACT

Various improvements are provided to breathing training, monitoring and/or assistance devices. A portable device is
(Continued)

provided which optionally includes a gas canister, a feedback system for implementing pressure control, and a visual output for indicating adherence to a breathing exercise to the user. The pressure control may provide regulation of different pressures for inhalation and exhalation.

7 Claims, 6 Drawing Sheets

(51) Int. Cl.
| | |
|---|---|
| A61M 16/10 | (2006.01) |
| A63B 23/18 | (2006.01) |
| A63B 71/06 | (2006.01) |
| A63B 24/00 | (2006.01) |
| A61M 16/20 | (2006.01) |
| A61M 16/00 | (2006.01) |
| A63B 21/04 | (2006.01) |
| A63B 21/00 | (2006.01) |
| A63B 21/008 | (2006.01) |

(52) U.S. Cl.
CPC .......... *A61M 16/12* (2013.01); *A61M 16/202* (2014.02); *A61M 16/208* (2013.01); *A63B 21/00069* (2013.01); *A63B 21/023* (2013.01); *A63B 21/0428* (2013.01); *A63B 24/0062* (2013.01); *A63B 24/0087* (2013.01); *A63B 71/0622* (2013.01); *A61M 16/0057* (2013.01); *A61M 16/101* (2014.02); *A61M 16/201* (2014.02); *A61M 2016/0027* (2013.01); *A61M 2205/3331* (2013.01); *A61M 2205/3546* (2013.01); *A61M 2205/50* (2013.01); *A61M 2205/502* (2013.01); *A61M 2205/582* (2013.01); *A61M 2205/583* (2013.01); *A61M 2205/587* (2013.01); *A61M 2205/8206* (2013.01); *A61M 2205/8237* (2013.01); *A61M 2209/086* (2013.01); *A61M 2230/40* (2013.01); *A63B 21/0087* (2013.01); *A63B 2024/0093* (2013.01); *A63B 2024/0096* (2013.01); *A63B 2071/0625* (2013.01); *A63B 2071/0655* (2013.01); *A63B 2071/0694* (2013.01); *A63B 2213/005* (2013.01); *A63B 2220/13* (2013.01); *A63B 2220/56* (2013.01); *A63B 2220/808* (2013.01); *A63B 2225/20* (2013.01); *A63B 2225/50* (2013.01); *A63B 2225/74* (2020.08); *A63B 2230/06* (2013.01); *A63B 2230/30* (2013.01); *A63B 2230/40* (2013.01); *A63B 2230/42* (2013.01)

(58) Field of Classification Search
CPC ... A63B 2024/0093; A61B 5/08; A61B 5/087; A61B 5/0871; A61B 5/0873; A61B 5/087509; A61B 5/097; A61B 5/093
See application file for complete search history.

(56) References Cited

U.S. PATENT DOCUMENTS

| | | | |
|---|---|---|---|
| 3,776,422 A | 12/1973 | Wise | |
| 3,949,749 A | 4/1976 | Stewart | |
| 3,981,301 A | 9/1976 | Warnow | |
| 5,360,000 A | 11/1994 | Carter | |
| 5,632,270 A | 5/1997 | O'Mahony | |
| 6,260,549 B1 | 7/2001 | Sosiak | |
| 6,273,088 B1 | 8/2001 | Hillsman | |
| 8,696,592 B2 | 4/2014 | Bingham | |
| 8,888,902 B2 | 11/2014 | Galbraith | |
| 2002/0096174 A1 | 7/2002 | Hill | |
| 2003/0183226 A1 | 10/2003 | Brand | |
| 2004/0154620 A1 | 8/2004 | Gale | |
| 2004/0249300 A1 | 12/2004 | Miller | |
| 2005/0028816 A1* | 2/2005 | Fishman | A61N 1/36003 128/200.24 |
| 2005/0205098 A1* | 9/2005 | Lampotang | A61M 16/12 128/207.18 |
| 2006/0125445 A1* | 6/2006 | Cao | H02J 7/027 320/112 |
| 2006/0157058 A1* | 7/2006 | Aylsworth | A61M 16/10 128/204.23 |
| 2006/0180149 A1* | 8/2006 | Matarasso | A61M 16/0069 128/204.18 |
| 2006/0292082 A1 | 12/2006 | Sarkar | |
| 2007/0074724 A1* | 4/2007 | Duquette | A61M 16/0012 128/204.18 |
| 2007/0089740 A1 | 4/2007 | Baumert | |
| 2009/0013996 A1* | 1/2009 | Rittner | A62B 9/027 128/202.22 |
| 2009/0227425 A1 | 9/2009 | Shirasaki | |
| 2010/0242975 A1 | 9/2010 | Hearn | |
| 2011/0195387 A1 | 8/2011 | Hsiao | |
| 2011/0284007 A1 | 11/2011 | Pierre | |
| 2012/0215124 A1* | 8/2012 | Fisher | A61M 16/208 600/532 |
| 2012/0247466 A1 | 10/2012 | Avni | |
| 2012/0298108 A1 | 11/2012 | Kane et al. | |
| 2013/0087146 A1* | 4/2013 | Callaghan | A61M 16/00 128/204.21 |
| 2013/0167843 A1 | 7/2013 | Kimm | |
| 2014/0137737 A1* | 5/2014 | Wilkinson | B01D 53/047 95/130 |
| 2014/0178844 A1 | 6/2014 | Warren | |
| 2014/0352690 A1 | 12/2014 | Kolb | |
| 2015/0059757 A1 | 3/2015 | Sardesai | |
| 2015/0136129 A1* | 5/2015 | Mahadevan | A61M 16/0003 128/203.14 |
| 2015/0283339 A1 | 10/2015 | Diacopoulso et al. | |
| 2015/0328417 A1* | 11/2015 | Löser | A61M 16/205 128/204.23 |
| 2017/0246420 A1* | 8/2017 | Callaghan | A61M 16/12 |
| 2017/0319812 A1* | 11/2017 | Truschel | A61M 16/201 |
| 2019/0282773 A1* | 9/2019 | Bambrilla | A61M 16/06 |

FOREIGN PATENT DOCUMENTS

| | | | |
|---|---|---|---|
| JP | 2926392 B2 | 7/1999 | |
| WO | WO9913931 A1 | 3/1999 | |
| WO | WO2004096110 A2 | 11/2004 | |
| WO | WO2008139380 A2 | 11/2008 | |
| WO | WO-2013179173 A1 * | 12/2013 | .......... A61M 16/204 |
| WO | WO2013179173 A1 | 12/2013 | |
| WO | WO2014003578 A1 | 1/2014 | |
| WO | WO2015054747 A1 | 4/2015 | |
| WO | WO15109259 A1 | 7/2015 | |
| WO | WO2015140553 A1 | 9/2015 | |

OTHER PUBLICATIONS

Peter Haidl et al., Inhalation device requirements for patients' inhalation maneuvers, 2016, Elsevier Ltd., pp. 67 (Year: 2016).*
"Sepration Design Group", Downloaded fro the internet Jul. 25, 2015 www.separationdesign.com.
"Helpful hints for filing", Downloaded fro the internet Apr. 19, 2018.

* cited by examiner

BREATHING TRAINING, MONITORING AND/OR ASSISTANCE DEVICE

CROSS-REFERENCE TO RELATED APPLICATIONS

This patent application claims the priority benefit under 35 U.S.C. § 371 of international patent application no. PCT/EP2016/074596, filed Oct. 13, 2016, which claims the benefit of European Application No. EP15192426.3 filed Oct. 30, 2015. These applications are hereby incorporated by reference herein.

FIELD OF THE INVENTION

This invention relates to apparatus and methods relating to monitoring or assisting breathing in patients.

BACKGROUND OF THE INVENTION

Over 1 Billion people suffer from respiratory diseases such as chronic obstructive pulmonary diseases, asthma, cystic fibrosis or neuromuscular disorders that affect patients' muscles and reduce lung function.

Chronic obstructive pulmonary disease (COPD) refers broadly to a group of conditions that cause irreversible respiratory impairment by increasing obstruction to airflow through the bronchi of the lungs. COPD typically has two components which may be present to varying degrees. The first is chronic obstructive bronchitis where the airways become reduced in volume, showing increased airway resistance making it more difficult to move air out of the lung. The second is pulmonary emphysema, where the small air sacs are ruptured causing air to be retained in the lungs and limit the available space during inhalation.

Individuals who predominantly have emphysema experience symptoms that differ in detail from those who predominantly have chronic bronchitis; however, both disorders contribute to shortness of breath during exercise and to general disability.

200 Million people worldwide suffer from COPD and it is predicted to become the third leading cause of death and disease worldwide by 2020, mainly due to its growing prevalence in developing and low income countries.

Chronic obstructive pulmonary disease is progressive and irreversible. It is an under-diagnosed, life-threatening lung disease that interferes with normal breathing. The primary cause of COPD is tobacco smoke. Other risk factors for COPD are indoor and outdoor air pollution, occupational dusts and chemicals.

The most common symptoms of patients with COPD are breathlessness, abnormal sputum with respect to volume and color, and chronic coughing. Breathlessness, or dyspnea, is the number one complaint by diagnosed or non-diagnosed COPD patients. Daily activities, such as walking upstairs can become very difficult due to breathlessness as the condition gradually worsens. Furthermore cough and getting rid of secretions that build up in the lungs is an issue for patients with COPD. COPD patients can be very prone to lung infections and pneumonia, which can cause a downward spiral of repeated lung infections and a further decline of lung function.

If symptoms are increasing, e.g. breathlessness or coughing, patients become anxious that their condition is deteriorating, especially patients living alone. Anxiety affects their quality of life as well as their health situation and contributes to worsening of their conditions, since with increasing anxiety patients become less active due to fear, e.g. to go outside alone or due to fear that they may run out of oxygen. With lower activity the condition of the patients worsens and the risk for hospitalization increases.

Acute exacerbations of COPD patients have a negative impact on their health related quality of life, pulmonary function and survival of patients with COPD. When COPD patients have an acute exacerbation, they are in most cases admitted to the hospital. They receive interventions such as non-invasive ventilation (NIV), medication treatment, and/or oxygen treatment to improve their conditions. At discharge, even if respiratory functions of the patients have been improved, most patients are nervous and anxious to be discharged to their home. Patients report that they do not feel better although the clinical judgment indicates this. Anxiety of being alone at home with the disease affecting patients them and does not support their recovery phase.

There is currently no cure for COPD patients and very few effective homecare solutions are available to alleviate symptoms.

There are a number of additional ways to assist such patients, and various such measures are described in this application.

It has been recognized that performing physical and breathing exercises can help to stabilize COPD symptoms and allow patients to get in control of their symptoms as part of disease self-management, also reducing the experience of anxiety.

This is addressed in pulmonary rehabilitation programs that are however only available to a limited number of patients due to the highly limited number of centers providing these programs as well as the associated cost and time off work. Furthermore, as they only last for a short time, the transfer of these exercises to the home situation and starting new, healthy habits might not be very efficient. Most patients quickly fall back into their normal and in most cases more passive lifestyle, which promotes a faster disease progression and deterioration. Consequently, even though applying simple breathing techniques could help them recover more quickly from shortness of breath, COPD patients will most likely not apply them.

By way of example, one breathing exercise is a pursed lip breathing exercise. The exercise begins by breathing in through the nose for about 2 seconds. Then the lips are puckered as if to get ready to blow out candles on a birthday cake. Breathing out slowly through pursed lips should take two to three times as long as breathing in. This exercise is typically repeated several times.

The pursed lip breathing technique slows down the breathing rate and keeps airways open longer so lungs can get rid of more stale, trapped air. It reduces the work of breathing, increases the amount of time patients can exercise or perform an activity and improves the exchange of oxygen and carbon dioxide. Normally, a patient can attain an exhalation (over) pressure level of 4 cm $H_2O$ (=382 Pa), whereas ideally, it should be 8 cm $H_2O$ (=785 Pa). The latter pressure level can be provided by a Positive Expiratory End Pressure (PEEP) or a Bilevel Positive Airway Pressure (BiPAP) device.

Another breathing exercise is a diaphragmatic breathing exercise. This is a more demanding exercise than pursed lip breathing and it is important that, before starting, the patient is relaxed and in a good position/posture to perform the exercise. Therefore it is important to take time to prepare before starting the exercise. To perform the exercise the patient is asked to place one hand just above the belt line, and the other on the chest, right over the breastbone to monitor the movement of belly and chest.

All the work should be done by the belly and the chest and shoulders should be more or less still. The next step is to open the mouth and gently sigh, as if someone had just told you something really annoying. This is to let go of all the air. During this exhaling step the shoulders and the muscles of the upper body should be relaxed, and fall down. Then the patient should close the mouth and pause for a few seconds. In the next step the patient is asked to keep the mouth closed and inhale slowly through the nose by relaxing the abdominal muscles and pushing their belly out. In the same time the waist and parts of the back can feel like expanding.

The movement of the belly precedes the inhalation by just the tiniest fraction of a second, because it is this motion (relaxation of the diaphragm) which is pulling the air in. When having inhaled as much air as is comfortable, without raising chest or shoulders, the patient is asked to stop and is finished with the inhaling. These actions can be monitored by tracking the motion of the belly and possibly the shoulders/chest by hand or via other means. After pausing briefly for whatever time feels comfortable, the patient is asked to repeat the exercise by opening the mouth and exhaling through the mouth by pushing in/contracting the belly and inhaling slowly as described above.

Training in breathing exercises such as those outlined above assists in breaking through the "vicious cycle" of disease progression through lack of exercise. During pulmonary rehabilitation, patients are educated about the disease and are trained on the breathing exercises as well as to be physically active. However, some patients do not have the possibility (availability, cost . . . ) to join such a program while others are not able to translate the learning into long term habits.

US 2014/0178844 discloses a breathing training system which can be used in the home, and thus attempts to address some of the problems outlined above.

The biggest problem of training breathing exercises is the adherence as the exercises have to become part of a daily routine to prove effective. Furthermore, the assistance of breathing exercises should be available in acute moments.

A training system should therefore have ease of use, have interactivity so that it is fun or engaging, give clear guidance but without drawing the attention of third parties, be personalized and optimized to suit the individual patient needs, and should give relevant feedback to the patient (together with their caregivers).

For COPD patients—and to a certain extend also for Asthma patients—breathing performance is indicative of the severity of the condition. The breathing performance is typically determined in a clinical practice by determining some of the following respiratory parameters:
1. Minute ventilation (VE)
2. Respiration frequency ($f_R$)
3. Breath by breath respiratory time ($T_{TOT}$)
4. Inspiratory time ($T_I$)
5. Expiratory time ($T_E$)
6. Inspiration to expiration time ratio ($T_I/T_E$)
7. Fractional inspiration time ($T_I/T_{TOT}$)
8. Cough
9. Flow estimation For example, a high $f_R$, low $T_I/T_{TOT}$ or low $T_I/T_E$ may indicate obstruction of a subject's airways.

Moreover, the delay of normal emptying of the lungs during expiration due to flow limitation, which is aggravated during exercise, leads to dynamic hyperinflation related to the increase in the respiratory frequency ($f_R$). This results in increased work of breathing, increased load on the respiratory muscles, and the intensified perception of respiratory discomfort.

It would be beneficial if at least some of these parameters could be recorded by a breathing training system to provide information of clinical relevance to the patient or to the patient's caregiver.

Apart from breathing training, another way to provide assistance to a patient is to deliver oxygen to the patient. When a patient experiences shortness of breath and needs such assistance (despite breathing training), there are various devices designed to provide such assistance.

Two main devices are used to combat shortness of breath in COPD (and other) patients.

A first is a Positive Expiratory Pressure (PEP) device, which produces the effect of a positive counter pressure upon exhaling by blowing through a restriction. For example a pursed lip breathing device is disclosed in WO 2004/096110. The pressure-flow rate relation of a restriction is super-linear, meaning that the pressure drops more than the flow rate does, tending towards lower values at the end of exhalation. While PEP may train the muscles, it does not prevent the closure of the lungs before complete emptying.

For optimal treatment of shortness of breath, a Positive Expiratory End Pressure (PEEP) is needed in combination with a long enough exhalation time.

It has also been suggested that inhalation through a restriction, to create an under-pressure upon inhaling, is also beneficial. This may for example apply when exercising with such a device. As mentioned above, pursed lip breathing is a known technique the patient can perform him/herself, but is limited to producing for example only 4 cm $H_2O$ pressure (=382 Pa), whereas for example 8 cm $H_2O$ is more optimal (=785 Pa). Of course, the desired pressure levels to be attained by the subject will depend on the nature of the subject, such as their age and their respiratory condition. These devices are cheap and may be paid out-of-pocket by the patients themselves.

An alternative approach developed by the applicant is a system (called "VitaBreath" (trade mark)) by which a patient blows against a blower upon exhalation, maintaining 8 cm $H_2O$ counter-pressure (=785 Pa) and upon inhalation delivers a positive pressure of 18 cm $H_2O$ (=1770 Pa). Details may be found in WO 2013/179173. The blower switches between the two pressure levels by rapidly changing a rotation rate. This device is relatively costly and therefore may be beyond the reach of the patients' budget, and can often only be acquired with reimbursement from health insurance.

COPD patients may suffer from both too high carbon dioxide levels and too low oxygen levels. The delivery of oxygen is known but only severe patients receive medical treatment with additional enriched oxygen flow rates starting from 1 liter per second, requiring expensive equipment.

Thus, although it is known that positive pressure support and oxygen can help to reduce the symptoms of COPD and other conditions, there is no small, lightweight, portable device available that can be used intermittently or only when needed, to rapidly reduce the shortness of breath during a normal daily activity such as vacuum cleaning, climbing the stairs etc.

It can be seen from the discussion above, that there remain several issues with existing systems for providing breathing training, monitoring and/or assistance. This invention relates to devices and method which provide solutions for at least some of these problems.

SUMMARY OF THE INVENTION

The invention is defined by the claims.

According to examples in accordance with an aspect of the invention, there is provided a portable breathing assistance or training device, comprising:

a housing which defines a mouthpiece;

a sensor arrangement for sensing breathing characteristics of a user;

an output indicator for providing output information relating to breathing instructions or exercises or to breathing performance and taking into account the sensed breathing characteristics;

a pressure control system for providing pressure control during exhalation to provide a positive end-expiratory pressure.

This aspect provides a portable device which is able to provide both training and assistance for breathing, for example by indicating how long to inhale and/or exhale, but also provide exhalation end pressure control.

Note that the term "assistance" is used to indicate that an output may be provided to the user to guide them in their breathing. In some optional examples, the assistance may extend to providing a source of gas (i.e. oxygen) for the user for emergency occasions.

The output information is for example to indicate adherence to breathing exercises, or to provide breathing training, or to indicate correct breathing performance, or to provide advisory timing information. In one example the output information is for instructing the user to breath at a certain rate, for example to inhale for a particular time period and to exhale for a particular time period. An instruction to exhale for a particular time period will take into account a reference breathing pattern for the user and the sensed breathing characteristics. The instructions then evolve over time to reflect the performance of the user.

The reference breathing pattern for example comprises breathing time and frequency but also it may take account of the flow or pressure.

The pressure control during exhalation enables pressure to be maintained throughout the exhalation cycle even when the final flow rate is low. Thus, there is a positive end pressure.

The device may further comprise a connector for receiving a portable source of pressurized gas, for providing gas to the user at a pressure above atmospheric pressure. In this way, the device also provides a supply of gas (e.g. air or air with enriched oxygen). The device then functions both as a training aid and an emergency device.

The pressure control system may comprise a controllable flow restriction between the mouthpiece and the ambient air. By opening or closing this restriction, the internal pressure within the flow channels of the device and which is present at the mouthpiece is controlled.

The pressure control system is for example for providing pressure control during both inhalation and exhalation, wherein the pressure control system is controllable to regulate different pressures during inhalation and exhalation. In this way, the device is able to provide training and assistance for both inhalation and exhalation and at appropriate pressure levels. The pressure levels may be different from patient to patient, and they may change with time and can be different depending on the use case (training or assistance).

The pressure control system may comprise a first valve between the gas canister and the mouthpiece, a second valve between the mouthpiece and a vent to ambient air and a pressure feedback path for controlling the second valve to regulate the pressure at the mouthpiece in dependence on whether the first valve is open or closed.

This provides a simple two-valve design which is able to regulate different inhalation and exhalation pressures.

The output indicator may comprise a light output device. This provides a simple visual indication of performance, for example in the form of a line of lights which progressively light up.

The output indicator may have at least two modes of operation, and the device comprises:

a configuration sensor for sensing a configuration of the device; and a controller for configuring the device to select the mode of operation of the output indicator in dependence on the output of the configuration sensor.

This feature provides an output to the user to provide training or assistance, but the output may be disabled or changed to a different mode in dependence on a configuration of the device. Thus user may for example want to use the device in a more discrete manner.

By way of example, one mode may be a visual output mode, and another mode may be a haptic output mode. The controller may then be for configuring the device to use the visual output indicator or the haptic output indicator in dependence on the output of the configuration sensor. In this way, the user can select between visual or haptic feedback.

The configuration sensor may comprise:

a tilt sensor for determining the orientation of the device; or a sensor for sensing a folded-out configuration or a folded-in configuration of the housing; or a sensor for sensing an extended configuration or a retracted configuration of the housing.

A visual output indicator for example comprises a line of LEDs which in use extend from the bottom of the field of view of a user to in front of the user's nose, wherein in one configuration the line of LEDs is in front of the user's face in use, and in another configuration the line of LEDs is below the user's mouth in use.

The device may further comprise:

a portable gas canister; or a portable gas canister for storing compressed gas, and a mixer for mixing the compressed gas from the canister with ambient air, wherein the mixer optionally comprises a turbine which is powered by the compressed gas to drive a fan.

The mixer may take the form of an injector or a fan and motor or a fan and turbine, wherein the fan is driven to draw in ambient air.

The portable gas canister for example has a column of between 0.2 and 1.0 L, for example between 0.2 L and 0.6 L The sensor arrangement may comprise at least a microphone.

A system may comprise the portable breathing assistance or training device as defined above and a portable display device for providing breathing exercise or training instructions to a user.

When the device uses a gas canister, it may be attached to a battery which is for supplying power to the rest of the device. This makes it possible to ensure that there is sufficient electrical power to operate the device, since the battery is replaced or recharged each time a new canister is used.

The system may further comprise a docking station for recharging the gas canister and also for recharging the battery when a rechargeable battery is used.

This aspect also provides a method of providing breathing assistance or training, comprising:

providing instructions for breathing exercises or training to a user;

sensing breathing characteristics of the user during the exercises or training;

providing output information relating to breathing instructions or exercises or to breathing performance and taking into account the sensed breathing characteristics;

regulating the pressure during exhalation at a first pressure level to provide a positive end-expiratory pressure.

This provides an assistance or training method which can be implemented by a portable device which enables a positive expiratory end pressure to be provided.

The method may further comprise, in response to user control, providing gas to the user during inhalation and may optionally further comprise regulating the pressure during inhalation to a different, second pressure level.

In this way, the device is able to provide pressurized gas for breathing support as well as providing breathing training.

This is for example for use in a crisis situation. Preferably, the user does not have to switch on the device to use it in this mode. The device may thus auto-power-on when it detects patient breathing. One option is to use sensors within the device by leaving them in a low power state, and when a certain threshold is achieved the device switches into full power mode. Alternatively, a passive actuator may be used to turn on when the airflow through the handset begins. This self-actuation could also extend to a wireless connection to a paired device, to share data or auto-connect at the same time, avoiding additional actions from the patient each time.

Breathing instructions may be provided to the user on a portable display device and the breathing characteristics are sensed on a portable breathing assistance or training device, with communication, such as wireless communication, between the devices.

The self-actuation mentioned above could also extend to a wireless connection to a paired device, to share data or auto-connect at the same time, avoiding additional actions from the patient each time.

Providing output information may comprise:

sensing a configuration of the device; and configuring the device to set a mode of an output indicator which takes into account the sensed breathing characteristics, for example setting the output indicator into a visual output mode or a haptic output mode, in dependence on the sensed configuration.

The sensing of a configuration may comprise:

determining the orientation of the device; or sensing a folded out configuration or a folded in configuration of the housing; or sensing an extended configuration or a retracted configuration of the housing.

According to examples in accordance with another aspect of the invention, there is provided a portable breathing assistance or training device comprising:

a housing which defines a mouthpiece;

a sensor arrangement for sensing breathing characteristics of a user;

an output indicator for providing output information relating to breathing instructions or exercises or relating to breathing performance and taking into account the sensed breathing characteristics;

a configuration sensor for sensing a configuration of the device; and a controller for configuring the device to select the mode of operation of the output indicator in dependence on the output of the configuration sensor.

This device provides an output to the user to provide training or assistance, but the visual output may be disabled in dependence on a configuration of the device. Thus user may for example want to use the device in a more discrete manner.

This aspect is not limited to a device which provides positive expiratory end pressure. A haptic output indicator may be used for providing the information relating to an adherence to a breathing exercise or training, wherein the controller is for configuring the device to use the visual output indicator or the haptic output indicator in dependence on the output of the configuration sensor. In this way, the user can select between visual or haptic feedback.

The configuration sensor may comprise:

a tilt sensor for determining the orientation of the device; or a sensor for sensing a folded out configuration or a folded in configuration of the housing; or a sensor for sensing an extended configuration or a retracted configuration of the housing.

There are various ways to configure the device into different modes of operation.

The visual output indicator may comprise a line of LEDs which in use extend from the bottom of the field of view of a user to in front of the user's nose. As the lights are illuminated, they become more and more clearly in the field of view of the user and in focus. In one configuration, the line of LEDs may be in front of the user's face in use, for example inclined away from the face so that the end of the device is easily in focus for the user, and in another in one configuration the line of LEDs is below the user's mouth in use.

The device may further comprise:

a gas canister for providing gas to the user at a pressure above atmospheric pressure; and a pressure control system for providing pressure control during inhalation and exhalation, wherein the pressure control system is controllable to regulate different pressures during inhalation and exhalation.

As in the first aspect, this enables breathing training and assistance to be provided using a single portable device.

A system comprises a portable breathing assistance or training device as defined above and a portable display device for providing breathing exercise instructions to a user.

This aspect also provides a method of providing an output from a portable breathing assistance or training device comprising:

sensing breathing characteristics of a user;

sensing a configuration of the device; and configuring the device to select a mode of operation of the output indicator in dependence on the output of the configuration sensor.

The configuring may comprise using a visual output indicator or else using a haptic output indicator in dependence on the output of the configuration sensor.

Sensing a configuration may comprise:

determining the orientation of the device; or sensing a folded out configuration or a folded in configuration of the housing; or sensing an extended configuration or a retracted configuration of the housing.

According to examples in accordance with another aspect of the invention, there is provided a portable breathing assistance device, comprising:

a housing which defines a mouthpiece;

a connector for receiving a portable source of pressurized gas for providing gas to the user at a pressure above atmospheric pressure; and a pressure control system for providing pressure control at least during exhalation to provide a positive end-expiratory pressure.

This device may be as simple as an emergence assistance device (with no training function, unlike the aspects above). It enables a portable device to provide breathing assistance by providing a positive end-expiratory pressure.

Note that the portable source of pressurized gas is a portable pressurized gas container and not a pipe for connection to a remotely located gas source.

The pressure control system may be further controllable to regulate different pressures during inhalation and exhalation.

The pressure control system for example comprises a first valve between the gas canister and the mouthpiece, a second valve between the mouthpiece and a vent to ambient air and a pressure feedback path for controlling the second valve to regulate the pressure at the mouthpiece in dependence on whether the first valve is open or closed.

This provides a two-valve arrangement for controlling the supply of gas canister gas as well as providing feedback regulation of two different pressures.

In one set of examples, the pressure feedback path is electrical and comprises a controller which receives a signal from a pressure sensor and one of two reference signals, wherein the reference signal depends on whether the first valve is open or closed, and the output of the controller controls the second valve.

This electrical system is simple to implement but requires electrical power.

In another set of example, the pressure feedback path is mechanical and comprises a biasing element which is controlled by the pressure at the outlet of the first valve and biases the second valve towards a closed position, wherein the bias of the second valve to the closed position with and without the bias of the biasing element is adjustable mechanically.

This provides a purely mechanical solution.

The first valve may comprise a manually operated user control. The user operates the valve when assistance is needed during inhalation. The system then automatically regulates the inhalation pressure to provide positive inhalation pressure (using the pressure of the source of pressurized gas) and which is higher than the regulated pressure during exhalation.

The device may further comprise:

a portable gas canister; or a portable gas canister for storing compressed gas, and a mixer for mixing the compressed gas from the canister with ambient air.

The mixer for example comprises a turbine which is powered by the compressed gas for driving a fan to draw in ambient air.

The portable gas canister may be attached to a battery, for example a rechargeable battery, which is for supplying power to the rest of the device.

In this device, a gas canister and a battery are combined, so that it can be ensured that gas and electrical energy are together supplied in a recharged state. In this way, the risk of a battery of the device running out of power is reduced.

The battery may be rechargeable so that it can be recharged when the gas canister is replenished (in the case of a reusable gas canister).

The gas canister and battery may be connected to each other in any way. The battery may be mounted on the outside of the gas canister or recessed into a cavity, or they may both be attached to a common frame. The battery may be removably attached to the canister The device may further comprise a second, rechargeable, battery within the housing, wherein the battery of the portable gas canister is for recharging the second battery.

Preferably the electrical energy of the battery attached to the canister should be consumed before the energy of the fixed battery is used. The fixed battery may for example be used without a gas canister loaded.

The device many further comprise:

a sensor arrangement for sensing breathing characteristics of a user;

an output indicator for providing output information relating to breathing instructions or exercises or to breathing performance and taking into account the sensed breathing characteristics.

This aspect also provides a method providing breathing assistance, comprising:

providing gas to a user at a pressure above atmospheric pressure using a portable device connected to a portable source of pressurized gas; and providing pressure control during at least during exhalation to provide a positive end-expiratory pressure, and optionally also to regulate different pressures during inhalation and exhalation.

The pressure control system may regulate the pressure during inhalation when a user activates a flow valve for releasing gas from the gas canister.

According to examples in accordance with another aspect of the invention, there is provided a gas supply system for a portable breathing or assistance device, comprising a gas canister and a battery connected to the gas canister for providing power to the portable breathing or assistance the device.

The gas canister and battery may be connected to each other in any way. The battery may be mounted on the outside of the gas canister or recessed into a cavity, or they may both be attached to a common frame.

The battery may comprise a rechargeable battery and the gas canister and the rechargeable battery are adapted to be recharged from a common docking station.

This aspect also provides a docking station for a gas supply system for a portable breathing or assistance device, comprising a socket for receiving a gas canister or a device having an attached gas canister, wherein the docking station comprises a gas delivery path to the canister and an electrical connection for recharging a rechargeable battery of the gas supply system.

The charging may be inductive or by direct electrical connection. A plurality of sockets may be provided each for receiving a respective gas cylinder or a device having an attached gas cylinder.

The docking station may have a modular design, for example it may be able to receive an oxygen concentrator module.

For example, the docking station may further comprise an oxygen concentrator module which is electrically powered by the docking station and operates a pressure swing adsorption oxygen concentration cycle using the pressure of the gas delivery path.

This aspect also provides a portable breathing assistance device, comprising:
  a housing which defines a mouthpiece;
  a connector; and
  a gas supply system as defined above removably attached to the connector for providing gas to the user at a pressure above atmospheric pressure.

In this device, a gas canister and a battery are combined, so that it can be ensured that gas and electrical energy are together supplied in a recharged state. In this way, the risk of a battery of the device running out of power is reduced. The battery may be rechargeable so that it can be recharged when the gas canister is replenished.

This aspect also provides a method providing breathing assistance, comprising:
  charging a battery and replenishing a gas canister of a breathing assistance device in which a battery is connected to the gas canister, using a shared docking station.

In all aspects above, the sensor arrangement may comprise a microphone.

Furthermore, in all aspects, a communication system may be provided for transmitting the sensor arrangement signals to a remote (display) device for setting and/or monitoring adherence to the breathing exercises or training. This provides a convenient system for the user. The communication may be over a wireless connection.

In all aspects above, when a gas canister is used, it may have a volume of between 0.2 and 1.0 L, for example between 0.2 L and 0.6 L. By mixing with ambient air, a small volume canister may be used to provide support for a reasonable length of time. This enables a small portable device to be created. The pressure of the canister is for example between 10 atm (1013250 Pa) and 20 atm (2026500 Pa).

In all aspects above in which the device provides a training function, an input may be provided to the system for receiving data from external monitoring devices such as monitors of heart rate, blood pressure, activity levels, stress levels, GPS data. This additional information may be used to improve the training or assistance provided.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides various improvements to breathing training, monitoring and/or assistance devices. A portable device is provided which optionally includes a gas canister, a feedback system for implementing pressure control, and a visual output for indicating adherence to and performance or execution of a breathing exercise to the user. The pressure control may provide regulation of different pressures for inhalation and exhalation as well as for different use cases or other input parameters, for example changes over time based on performance levels and/or doctor advice.

A first aspect relates to breathing training, and provides a system for home use, which is designed as a modular system for providing guidance, motivation and confidence to apply breathing techniques advised to COPD (or other) patients. The system is for providing support and guidance during the training of breathing exercises.

In addition, in some implementations it acts as an intervention tool in acute moments of shortness of breath, e.g. after physical activity. By then helping the patients to regain their normal or optimal breathing rhythm more quickly, it helps them to stay more active. The system can be extended and adjusted according to the patient's need to serve them optimally during the different phases of the disease.

Figure 1:
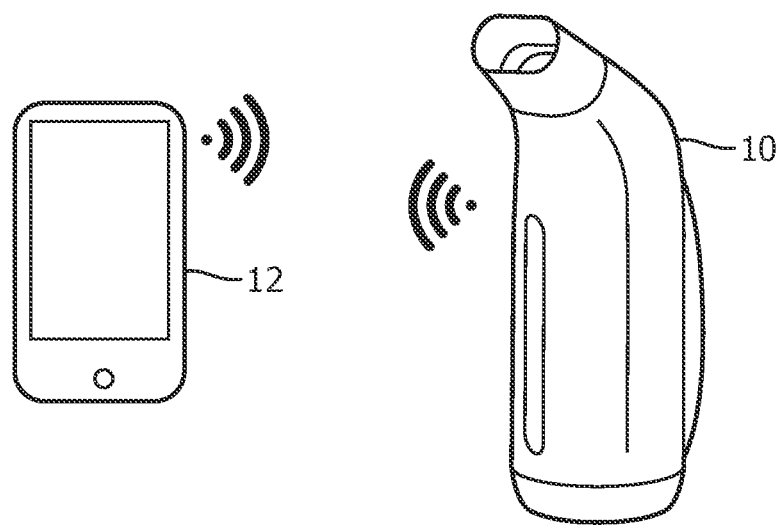
FIG. 1 shows a portable breathing assistance or training device.

The system is shown in FIG. 1. It comprises a portable breathing assist device 10 used to support COPD patients in the exercise and application of breathing techniques, and a remote display device 12 which provides a user interface. The display device 12 is shown as a smart phone on which an app is loaded so that the display device 12 communicates wirelessly with the breathing assist device 10. The display device may connect to a remote platform hosting services to provide extended functionality and services.

The breathing assist device comprises a housing which defines a mouthpiece as shown. Within the housing is a sensor arrangement for sensing breathing characteristics of the user.

In a most basic implementation, a device is used to measure breathing rate of the user, and provide feedback to the user, while additionally providing pressure feedback so that the system provides a positive expiratory end pressure.

In more advanced implementations, a gas canister is housed in the base of the housing, for providing gas to the user at a pressure above atmospheric pressure, for assisting the user during acute events.

The pressure feedback system may then also provide pressure control during gas delivery which takes place during an inhalation cycle.

The user interface can be realized in different ways. The display device 12 may be used on its own to practice breathing exercises, with options for up-grades. The breathing assist device 10 may also be used on its own used to give feedback about breathing exercises, to support breathing, and also provide positive pressure support during exhalation (PEEP).

The two devices may be used together to offer more options, for example exercises which take the form of games or other entertaining or engaging ways to encourage the correct performance of the exercises. The overall system can also provide more precise data collection, for example measuring flow as well as breathing events. The app on the display device can act as a data collector and connection to a remote platform, although this can be integrated in the breathing assist device 10.

The system is designed to deliver an optimized training and intervention experience. By collecting data on the execution, performance and frequency of use a patient history can be established that helps to monitor the status and progression of COPD.

To provide active breathing training, the system is preferably adapted to measure breathing related parameters, such as breathing rate/breathing pattern, flow, overall exhaled volume, attained pressure, etc., and to determine irregularities and fluctuations in these parameters.

The device can operate in different modes.

In a training mode, an indication can be provided of the time during which the patient should be exhaling and/or the pressure that should be reached, and an indication of whether these targets are met. The user interface for example also provides guidance and support for applying pursed lip breathing. In general, the system can measure the performance and effectiveness of the breathing exercises and provide appropriate coaching.

In a mode where the system is used to overcome a shortness of breath e.g. induced by physical activity, the system can provide an evaluation of the initial breathing rate range (e.g. red for very fast breathing). The scale may depend on previous usage, so that the system is implemented as a self-learning system.

The indication for the time of exhalation may be slowly increased, to slow down the patient's breathing.

The system can be configured to suit the individual patient's needs and the patient profile. It can store all data relating to the use of the interface, and can connect to a platform to which it can forward the data for further processing and feedback to additional parties.

A first function of the system is to provide breathing guidance with the breathing assist device, and to provide assistance when there is an acute moment of shortness of breath:

During a physical activity COPD patients experience shortness of breath. To regain their normal breathing rhythm they use the breathing assist device. The breathing assist device first measures the breathing rate and compares this with the "normal" or "preferred" setting. Depending on the severity or possible previous data gathered for this particular user, i.e. discrepancy from the "normal" setting, the rate of slowing down the breathing is predicted.

This information is used to set by how much the breathing should be slowed down from one breath to another, e.g. 5% longer, as well as when the guidance is stopped, e.g. five or ten repeated "normal" breathings.

The breathing assist device may indicate too fast breathing to the user by providing an indication such as a low volume but high pitch sound, a red light, or a fast vibration. This signal will change as the breathing is slowed down, either to a lower pitch sound, a yellow-green light or a slower vibration respectively. The signal will disappear once a normal breathing pattern has been regained. Optionally, in addition to this qualitative indication a more quantitative guidance can be implemented on the breathing assist device tool or on the display device.

The user may be invited by the system to cough after a number of breaths, or if irregularities, fluctuations or noise are detected.

Figure 2:
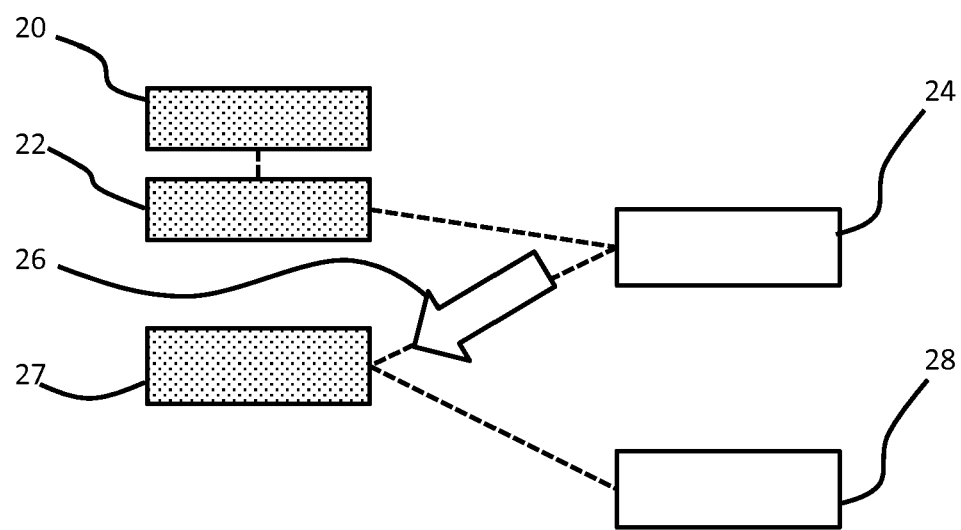
FIG. 2 shows a method of providing breathing assistance.

FIG. 2 shows the sequence of events. The left column of shaded boxes relates to actions or events which relate to the patient and the right column of un-shaded boxes relates to actions or events which relate to the breathing assist device 10 (or the display device).

In step 20, the patient performs physical activity. In step 22 the patient experiences shortness of breath and decides to use the breathing assist device 10. The breathing assist device 10 then in step 24 measures the breathing rate, compares this to a normal rate (for that particular patient) and determines the appropriate slow down rate for the breathing. The required breathing rate is then indicated to the patient as shown by arrow 26. In step 27, the patient slows down their breathing as guided by the breathing assist device 10. The patient's breathing rate is monitored in step 28 to measure the improvement.

In one version, the breathing assist device 10 is also able to deliver positive pressure breathing support. This may for example accompany the guidance to slow down the breathing rate (arrow 26). The positive pressure breathing support may for example increase gradually as in an acute situation additional pressure might be experienced as an additional burden.

By way of example, the breathing rate instruction may initially be decreased and at a certain moment the pressure is increased for an optimized effect.

In addition, data is gathered about the patient performance for feedback to the patient or to a caregiver.

Note that the instructions to the patient may be relayed by the breathing assist device as explained above, or by the display device, or both.

A second function of the system is to provide breathing exercise training.

Figure 3:
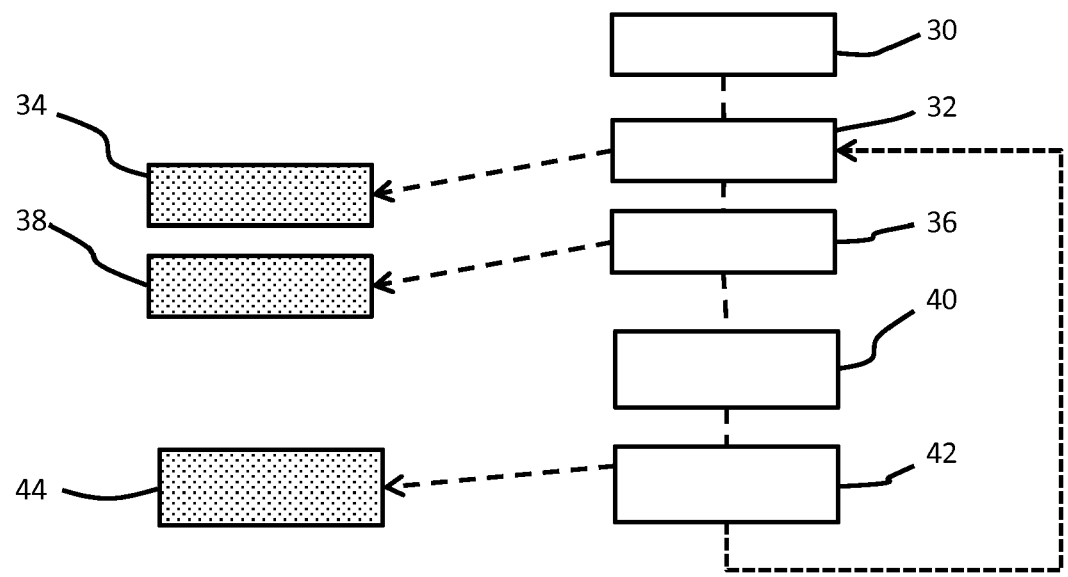
FIG. 3 shows a method of providing breathing exercise training.

FIG. 3 shows the sequence of events. The left column again relates to actions or events which relate to the patient and the right column relates to actions or events which relate to the breathing assist device (or the display device).

The app is started in the display device 12 in step 30 and base parameters are established, such as the background noise, normal breathing rate, etc. The breathing parameters, such as inhalation and exhalation time, flow etc. can be measured using various different sensors such as a flow meter, a microphone possibly attached to the chest, accelerometer attached to the belly, an accelerometer in a smart watch on the wrist, with the patient requested by the smart watch to place the hand on the belly, etc.

The goal of the exercise is to achieve a long exhalation time. This is either a pre-set time depending on the patient's status, e.g. 4-10 sec., or a time established with respect to the base parameters and a pre-set factor, e.g. 2 or 3 times as long. The exercise is repeated several times, e.g. 5-10 times, depending on recommended settings by the doctor (or therapist) or an experience value.

In step 32, the display device indicates to the user the instructions to be followed. The exercise starts with a request provided to the patient to inhale. The patient inhales in step 34. Afterwards a goal is indicated to the user in step 36 that the patient has to reach by exhaling for the pre-set amount of time. During the exhalation shown as step 38, an indicator advances towards the goal to show the patient the progress. This can be implemented in either a rather simple, technical visualization e.g. a line that moves towards the goal line or the second indicator of a watch moving towards a marked time. It can also be visualized in a more fun way, using gaming type approach for example inflating a balloon to a certain size, blowing out candles on a cake with one candle extinguishing per second exhaled or advancing a ball across a goal line, etc.

Step 40 is the display of the advancement towards the goal.

Breathing exercises with the breathing assist device 10 alone can be implemented in a similar way, with the indication on the exhalation duration coming directly from the tool, e.g. by sound, visual or haptic indications.

In step 42, if the goal was reached, a next inhale exhale procedure is started, as shown by the feedback loop to the instruction step 32. If the goal was not reached, a next inhale exhale procedure is started but more time might be allocated for the inhaling. This might be used if the goal has been missed repeatedly. Furthermore, only more time for inhalation is given and the time for exhalation (which was not met previously) may be kept the same. Other events may also be detected such as coughing, in which case a period may be set to allow the patient to recover or the exercise might be interrupted completely.

There may be further instructions to the user in step 44 such as a questionnaire to determine how the patient feels or perceived the exercise. Alternatively, step 44 may relate to another type of breathing exercise. For example if starting with pursed lip breathing, this could be followed by diaphragmatic breathing which is done in a similar way, but recoding different parameters. The exhalation time may be adjusted as this is a more difficult exercise.

Depending on the patient's status as well as the disease progression, the user interface can be extended. For example, an extended exercise portfolio may be provided, for example to include diaphragmatic breathing with either an additional device or video analysis to track the belly and possibly the chest and shoulder movement. Different levels of data analysis and feedback may be provided as well as services e.g. for additional information and coaching, as well as direct feedback to a doctor. The system may also implement data collection from additional devices.

The collected sensor data may be evaluated (by a doctor, off-line) in the context of the breathing exercise. The breathing parameters can be significantly different depending on the type of breathing exercise, e.g. for COPD patients diaphragmatic breathing is more difficult to do well and not to start coughing than for pursed lip breathing.

Different settings may be used, for example pursed lip breathing could be performed without a target exhalation duration or an initial, pre-set time to just monitor the overall performance without guidance.

Furthermore, based on the data input, the exercise settings can be adjusted dynamically during one session or from session to session. So, rather than just guiding, a smart solution is possible. For example, if a lot of coughing occurs, and exercise has to be stopped. If the exercise repeatedly cannot be performed well or is performed with ease, then the settings can be adjusted.

Hence, a feedback loop exists in the system control is part of the exercise (game) control unit. For a system without data collection, the breathing exercise settings would have to be set manually, e.g. in discussion with care providers. With collection of sensor data, this can be automated, based on the recorded data which makes it more convenient to use and also gives a lot of test data to the doctor.

In this way, a breathing exercise may be set in a smart way, using analysis of the sensor data (e.g. sound) plus possible other input data, so that medically relevant data can be obtained which is not really obtained in any other straight forward way.

As mentioned above, the system can provide positive end pressure support during exhalation and inhalation (BiPAP).

Figure 4:
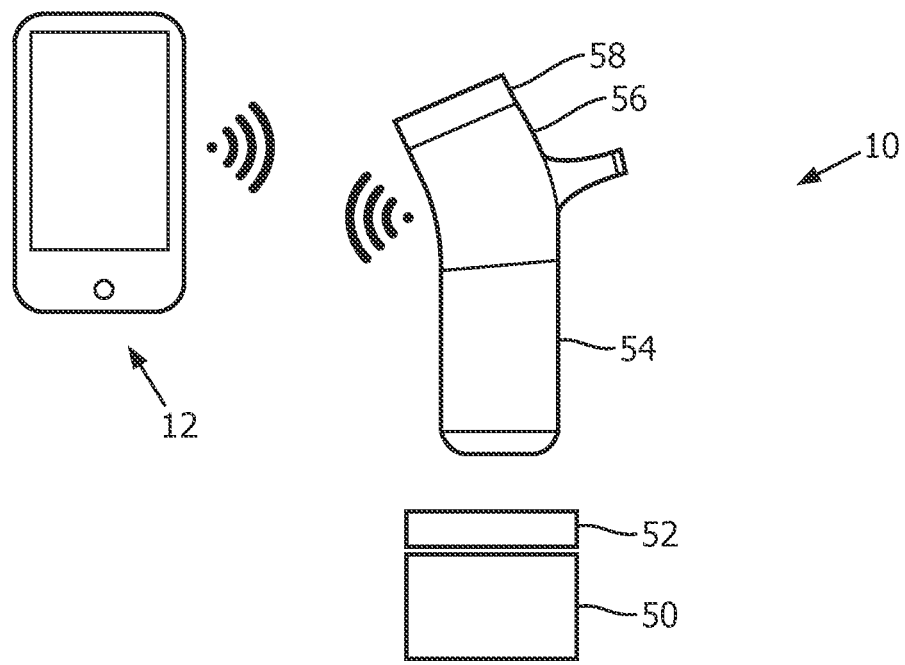
FIG. 4 shows a portable breathing assistance or training system.

FIG. 4 shows the general system.

It comprises a charging station having an air charging unit 50 and an oxygen charging unit 52. They may be stacked one over the other (in either order) or side by side. The breathing assist device 10 comprises a canister 54 for canned air or canned air enriched with oxygen. It may be for almost pure oxygen, then to be mixed with ambient air.

The charging station may include electric charging. Air or oxygen enriched air is provided to a patient, for example with a maximum oxygen concentration of about 40%. Pure oxygen is not provided to a patient. If nearly pure oxygen comes from a canister, it is mixed with ambient air.

The main head 56 of the breathing assist device 10 provides sensing of breathing parameters as well as the controlled delivery of the positive pressure to the patient. An optional module 58 is also shown with medication (RDD) so that the device functions in a similar way to an inhaler. The various parts can be modular so that different combinations of units may be employed. Thus, the modules can be used either via a simple tool without data connection to a remote device, or as a smart tool that also collects data and connects with the app, as shown in FIG. 4. A patient may thus build the modular system starting from the breathing assist device or the display device app, and may also decide to extend or upgrade to a positive pressure BiPAP device with a controller module.

The system includes a pressure control system for providing pressure control during inhalation and exhalation, wherein the pressure control system is controllable to regulate different pressures during inhalation and exhalation. Some examples of suitable pressure control systems are described further below.

The overall system can be extended to connect with additional data sources that deliver data to the app or the platform. These additional devices for example comprise monitoring devices and modalities e.g. heart rate, blood pressure, activity, stress, questionnaires, GPS data (location, direction, velocity and distance), etc.

The device may implement an electronic diary and provide web-based information such as weather conditions and air quality.

Additional devices can for example enable additional breathing exercises such as diaphragmatic breathing as outlined above. Furthermore, additional data can be used to extend the information that can be used for monitoring allowing better insights in the patient's status and hence delivering better feedback and coaching.

The sensing used in the breathing assist device may provide data which can then be analyzed to extract information on the performance (and progression of performance) during and effectiveness of breathing exercises, and adherence to the exercises. The history of usage of the device for training or for intervention is recorded.

Based on this data, intelligence is gathered about the individual patient's situation so that triggers, application settings, coaching options and presented information can be adjusted. Furthermore, long-term changes are identified for disease self-management and status of disease progression.

Certain parts of the information gathered by the system can be provided to third parties including the system provider, relatives and friends (i.e. users of the social community), any informal or formal caregiver, insurance providers and healthcare providers e.g. doctor or nurse.

For example, adherence information may be used by insurance companies or by caregivers. The information exchanged may include not only the sensor data of the breathing assist device itself, but also any other monitoring devices used by the patient.

As mentioned above, the system in some implementations is able to deliver a positive pressure. Currently, PEEP devices provide positive pressure during exhalation, but no guidance for the patient for how long to exhale.

Another example relates to a visual interface consisting of a series of light sources such as LEDs which can be programmed to light up in a certain color.

Figure 5:
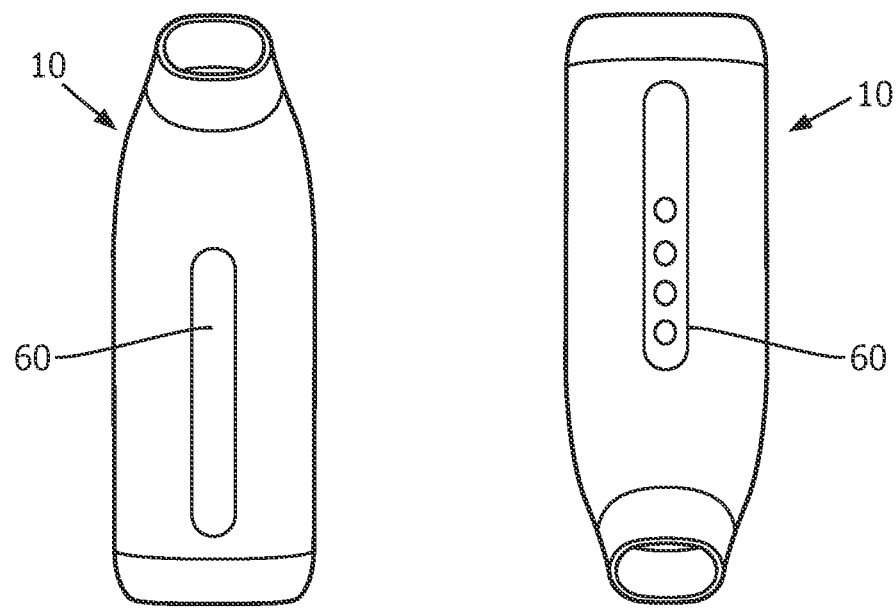
FIG. 5 shows the portable breathing assistance or training device in two different configurations.

The breathing assist device 10 is shown in FIG. 5, with a line 60 of LEDs running parallel to an elongate axis of the device, functioning as an output interface to the patient. The breathing assist device is designed to point slightly upward in use, such that the interface 60 comes in the line of sight of the patient and the end of it in focus. The longer the patient exhales, the more and/or further away LEDs light up during exhalation (e.g. in white or yellow). The maximum time is marked with a different LED color (e.g. green), and the patient is incited to try to improve his previous result by exhaling longer, until a pre-set optimum time is reached. A last LED may be used in yet another color (e.g. red or purple) to indicate that the patient is overdoing it.

The display is reset if no exhalation is measured for a prolonged time such as more than 10 seconds. As example above, the data may be collected and sent to an app on the display device 12.

The app running on the display device 12 may have a visual display looking substantially the same as the LED array on the breathing assist device. The display on the app may be fed with the data coming from the breathing assist device, but alternatively also with sound analysis of the exhalation of a patient who is near the app.

In order to determine exhalation, so that the exhalation may be timed, an electrical contact switch is provided on a spring operated valve (as used in Threshold PEP devices), or a pressure sensor in the mouthpiece may be used, in either case to detect exhalation at a sufficiently high pressure. A controller measures the signal and controls the programmable strip of LEDs.

This approach provides a visual interface. In a public situation the patient may want to use the breathing assist device 10 without the visual interface lights on, and use the device as discretely as possible. Moreover, some users may find that the closeness of the LEDs which may therefore be out of focus (depending on the eyesight of the patient) is an inconvenience with the visual display. The visual interface is designed such that it can still be interpreted when out of focus. However, some patients may prefer an alternative feedback mechanism.

In one aspect therefore, the portable breathing assistance or training device has a visual output indicator on the housing for displaying information relating to an adherence to a breathing exercise or training. A configuration sensor is used to sense a configuration of the device, and a controller then configures the device to use the visual output indicator in dependence on the output of the configuration sensor.

In this way the visual output indicator may be disabled if the user wants more privacy. There may then be a haptic output indicator for providing information relating to an adherence to a breathing exercise or training, which may be used instead.

In a first variation, the device designed to recognize when it is rotated over 180 degrees around the horizontal axis running through the mouth. A tilt sensor is used to determine the orientation of the device, such that in the discrete position of the device pointing downwards, the lights of the visual display are turned off, and the patient experiences haptic feedback. This can be achieved by operating a small motor within the device to generate a vibration, in known manner. Thus, there is automatic selection between a haptic feedback mode (such as vibration) and a visual feedback mode.

In FIG. 5, the left image shows the breathing assist device in haptic mode and the right image shows the device in visual feedback mode.

In a second variation, the output interface 60 is in a part of the breathing assist device body which can slide out, such that the device is extended and a larger part of the display is in focus. The visual interface only lights up if the display is activated by a switch/electrical contact when the display is in the extended position.

In a third variation, the display may be at least partially on a part of the breathing assist device which can be folded out. Again, the visual interface only lights up if the display is activated by a switch which detects when the display is in the position of maximum unfolding. In this variation, the visual interface can be on a flexible display, with halves on both parts of the breathing assist device, namely the solid part held in the hand, and the rotated or rolled out part.

The mouth piece may be designed such that it is symmetric when rotated by 180 degrees, or else it can be designed to rotating relative to the device.

Thus, a tilt sensor for detecting rotation, or else a switch which is activated upon unfolding or extending the device, is used to activate a visual display, or else select between visual and haptic feedback.

As mentioned above, there are various parameters which may be used as an indicator of breathing performance. Breathing exercises implemented as instructions provided on mobile devices are very suitable to relieve anxiety and shortness of breath as explained above. When only using a mobile device (rather than a full sensing breathing assist device as explained above), it is not clear to the user to what extent such exercises are effective and nor do these devices help to monitor the mid and long-term progression of the breathing condition (COPD or Asthma). Such monitoring requires measurement of at least some of the breathing parameters which then typically requires a visit to a clinician. Hence the patients are often not motivated to keep up the exercises as they cannot see the short term effects.

By tracking breathing parameters over time as explained above, progression of the breathing condition is established. This reduces the need to visit the clinician and yields improved accuracy as the amount of instances at which these parameters are measured is increased.

With the exception of flow, the respiratory parameters listed in the introduction above can each be derived from a microphone audio signal when the user is breathing towards the microphone. Thus, breathing exercise applications on mobile devices may be extended by analyzing an audio signal and extracting respiratory parameters. Direct feedback can be given to the patient as well as providing a clinically relevant report on the progression of the breathing condition.

Similarly, a microphone may be used as a parameter sensor as part of the breathing assist device 10.

Figure 6:
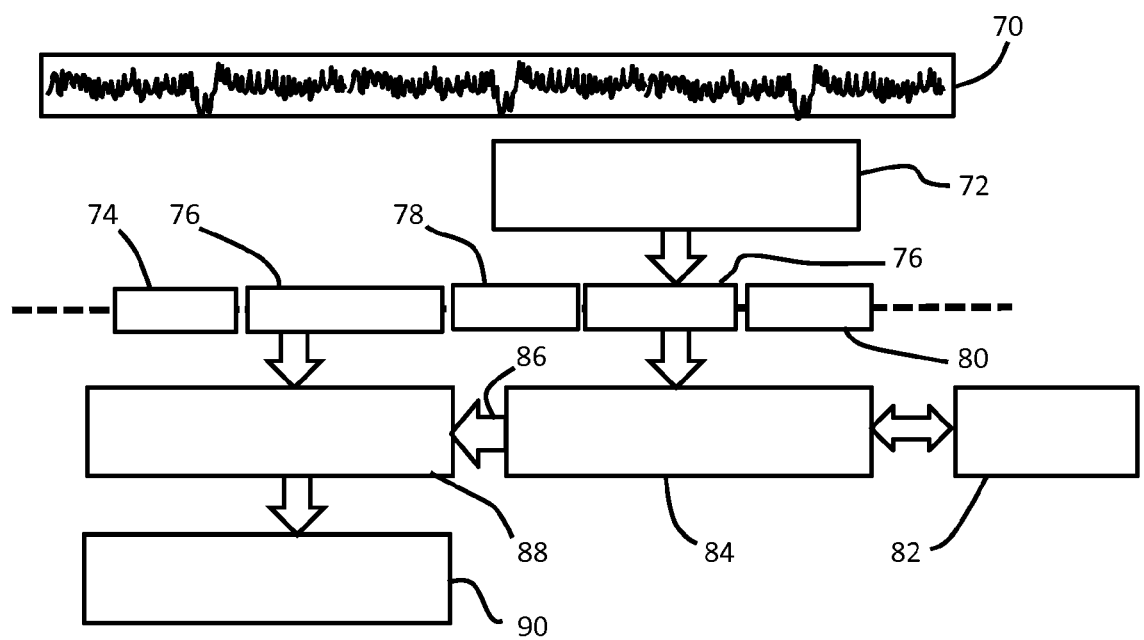
FIG. 6 shows a method of analyzing an audio signal to extract breathing parameters.

FIG. 6 shows a method which makes use of a microphone for providing user feedback.

The breathing exercise application analyses an audio signal 70 in step 72 and converts it to a stream of audio events, such as an in breath 74 an out breath 76, a pause 78 and a cough 80.

These events control the breathing exercise logic 84, guiding the user through the user interface 82 (e.g. the display device 12) and controlling the exercise, for example in a game-based way as explained above.

In parallel, the audio events are analyzed by the respiratory monitor and respiratory parameters are extracted in step 88 and stored in a report in step 90.

The audio signal 70 is the output of a microphone that picks up the user's breathing. Both the breathing exercise routine and the respiratory monitor routine use the audio events for further analysis. The breathing exercise uses the audio signal for direct real time feedback, whereas the respiratory monitor logs the overall performance over the short and long term. Relevant information may for example be the number of coughs per exercise session, the number of exercise repetitions, the number of repetitions executed well, trends during the exercise session and over multiple exercise sessions.

In addition, extra cues 86 about the audio events are sent from the breathing exercise control logic 84 to the respiratory parameter extraction function 88. For example, a breath out event can be due to pursed lip breathing, as instructed by the breathing exercise, and this hint can be used by the respiratory monitor routine to start extracting a respiratory parameter such as the increase in $f_R$ directly after pursed lip breathing.

The extracted respiratory parameters are placed in context in a respiratory report, that is then stored to derive trends or to share with a clinician.

As discussed above, providing a positive inhalation pressure is one approach to alleviate shortness of breath, and some implementations of the training and monitoring system described above provide this functionality.

This aspect relates to a way to occasionally produce the additional benefits of a positive pressure during inhalation in a low cost, small, lightweight, portable device, while maintaining the most important effect of having a positive exhalation pressure.

Additionally, it is then possible to provide enriching with oxygen, which helps especially with exercise-induced desaturation and the resulting shortness-of-breath. This is particularly common. The combination of positive end expiratory pressure (PEEP) and occasional positive inspiratory pressure (PIP) increases the tidal volume and reduces the work of breathing during an acute episode of dyspnea and reduces the related anxiety.

An episode of shortness of breath usually lasts only a few minutes, and usually patients who experience this have no means of acutely relieving this, even when they know it is coming, leading to panic. The reverse is true too: panic may lead to shortness of breath, thus creating a vicious circle.

A response from inhaling medication is often not quick enough. Training of the lungs, lips and psychological techniques may help using the system as described above, but this requires extensive training, and may be forgotten in case of an acute event. The short duration of such an event leads to the insight that the number of breaths during such an event as quite limited, and that quite a number of them can be supplied with positive pressure, coming from a canister filled with pressurized gas.

As explained with reference to FIG. 4, the gas may be air, oxygen enriched air, or highly enriched oxygen which is then mixed with ambient air.

Figures 7, 8:
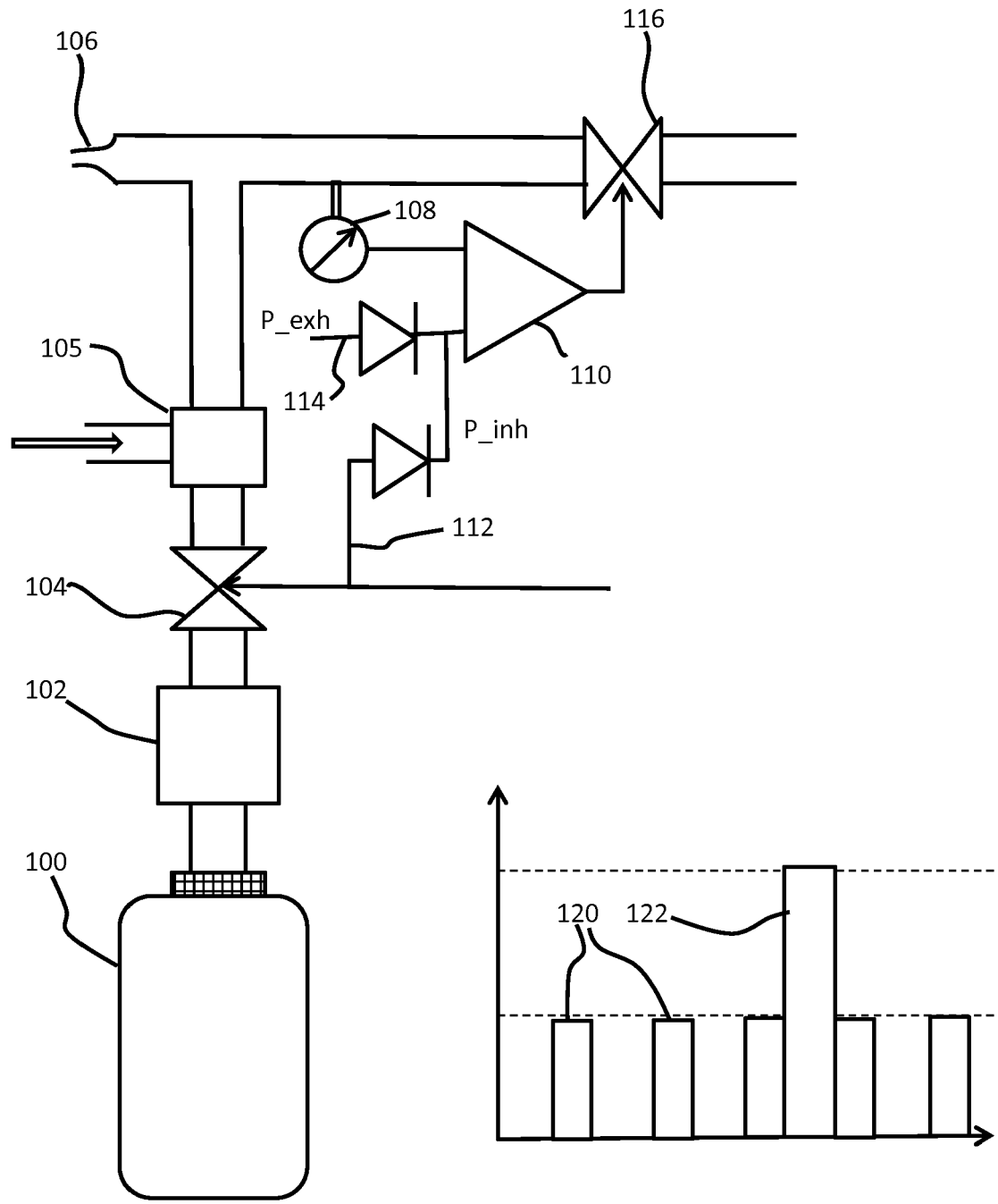
FIG. 7 shows a first example of pressure control system.
FIG. 8 shows a pressure time graph for the device of FIG. 7.

FIG. 7 shows schematically the functional parts of a first example of device for delivering positive air pressure from a small portable canister.

The device comprises a canister 100 in the form of a small pressurized gas bottle. It typically has a volume of 0.2-0.6 L of compressed gas at a maximum pressure of for example 10 atm (1013250 Pa). The output from the gas bottle is connected to a pressure control device 102. In the case of a canister of pressurized air or oxygen enriched air, this comprises a pressure reducer so that the pressure is controllable to a pressure level below the pressurization level. In the case of a canister of enriched oxygen, an injector 105 is provided (either as well as the pressure reducer 102 or instead of it) which is used to mix the oxygen with ambient air.

The outlet from the pressure control device 102 passes through a user controlled valve 104 such as a lever operated valve. The pressure control device for example is used to safely decrease the high canister pressure down to the near ambient atmospheric pressure.

The valve 104 may be of the type used for pressurized oxygen cans, but with the additional feature that upon moving the lever, it also activates a change in the feedback control system described below.

The outlet from the valve 104 passes to the mouthpiece 106 (with injection of ambient air if the injector 105 is needed). The pressure in the tube near the mouthpiece is monitored by a pressure sensor 108, which generates a pressure sensor signal which is provided to a first terminal of a controller, which in this example is shown as a differential amplifier 110. The use of an amplifier circuit provides a simple low cost circuit. The controller may instead be implemented as a processor such as a digital signal processor, which receives the input signals at an analogue to digital converter port. The settings of the inhalation and exhalation pressures p_inh and p_exh may then be adjusted dynamically, even per breath, depending on the analysis of the breathing pattern of the patient during exercise or intervention.

The other terminal of the controller circuit receives one of two possible reference signals. A first higher voltage signal 112 is generated when the lever 104 is open, and it corresponds to an inhale pressure for example of 18 cm $H_2O$ (=1770 Pa). With the lever closed, a second signal 114 is used as the reference, and it corresponds to an exhale pressure for example 8 cm $H_2O$ (=785 Pa). The higher voltage signal overrides the lower voltage signal when the lever is opened as a result of a diode or other circuit arrangement.

The controller generates a control signal to implement feedback control which sets the pressure near the mouthpiece to the reference level, by controlling an electronically operated valve 116 which is coupled between the mouthpiece and the outside.

The valve 116 functions as a restriction through which air is blown. The valve is controllable to different settings, for example opening progressively as the control voltage is increased.

The device is able to provide an occasional positive inspiratory pressure (PIP) during the inspiratory phase, while maintaining the PEEP levels (e.g. 4-30 cm $H_2O$=392-2940 Pa).

The PEEP and PIP pressure settings can be adaptive rather than fixed. They can be manually controlled and regulated by the patient depending upon his requirements and comfortable levels. Alternatively, they may be automatically adapted according to the detected respiratory rate, respiratory phases, respiratory variability etc., if additional sensors are integrated in the device. Moreover, these monitored parameters may be sent wirelessly to an intermediate app or user interface to be shared with the caregivers or clinicians. The device may for example be separable into two independent modules to provide only exhalation support (PEEP) or the combination of PEEP and PIP.

A device which supports only a PEEP function may for example be used as a training device as an alternative to pursed lip breathing (PLB), when the pressure is set to a minimum level such as 4-5 cm $H_2O$ (392-491 Pa).

The canister may be a small pressurized gas bottle for example less than 1 L, less than 0.6 L and possibly as small as 0.2 L, which can be carried separately and can be connected to the PEEP unit when needed.

The system is able to providing a preferred counter pressure upon exhaling such as 8 cm $H_2O$ (=785 Pa); no or negative pressure upon inhaling, and upon action of the patient, providing a stable higher pressure such as 18 cm $H_2O$ (=1770 Pa), during inhaling.

An injector or mixer may be used not only for enriched oxygen but also for all other types of compressed gas, for example in order to be able to deliver the maximum number of breaths by taking in ambient air.

In use of the system, the patient takes the mouthpiece 106 at the front end of the delivery straw into the mouth when exhaling. Upon reaching the required pressure level (p_exh), the pressure sensor 108 gives a sufficiently high voltage to open the electronic valve 116, to maintain the pressure. For the example of a differential amplifier, by setting the gain level of the amplifier 110, together with the pressure-flow characteristics of the valve, it is possible to have a comfortable effect for a patient that cannot reach the optimum pressure, yet has to be able to exhale.

Upon inhaling, the patient may choose to do either of two actions:
(i) Open the mouth to take a large breath, also having the effect that the pressure in the straw drops to zero, and the electronic valve closes to its minimum opening.
(ii) Every once in a while, the patient may time the pressing of the lever of the user operated valve 104, while keeping the mouthpiece tight with the lips. Air is flowing into the straw, while at the same time the electronic signal is given to maintain the pressure in the straw at a higher level (p_inh).

A typical pressure-time plot is shown in FIG. 8. The small peaks 120 are exhale pressure spikes, and the large peak 122 is when the patient applies the lever while Inhaling.

There may be an additional valve in the mouthpiece straw, such that the user also inhales through the straw, and has (slight) under-pressure upon inhaling. This has the additional advantage that the coordination required from the patient is less.

The user operated valve 104 may also be replaced by a machine operated valve, for example which opens every once every predetermined a number of breaths, further diminishing the coordination required from the patient.

The system may make use of other sensors, for example physiological parameters such as respiratory rate, respiratory rate variability, $SpO_2$, $pCO_2$, activity rate etc., may be obtained from any wearable device. These sensor signals can then be fed back to the device to optimize the pressure support or the oxygen content in the respiratory phases.

The system of FIG. 7 has an electronically controlled valve 116. An alternative simpler design can be purely mechanical, driven by the same pressurized gas. The disadvantage of the electronic design is that additional electrical power from a battery is needed so that (more) regular recharging replacement or inspection of the battery is required.

Figures 9, 10:
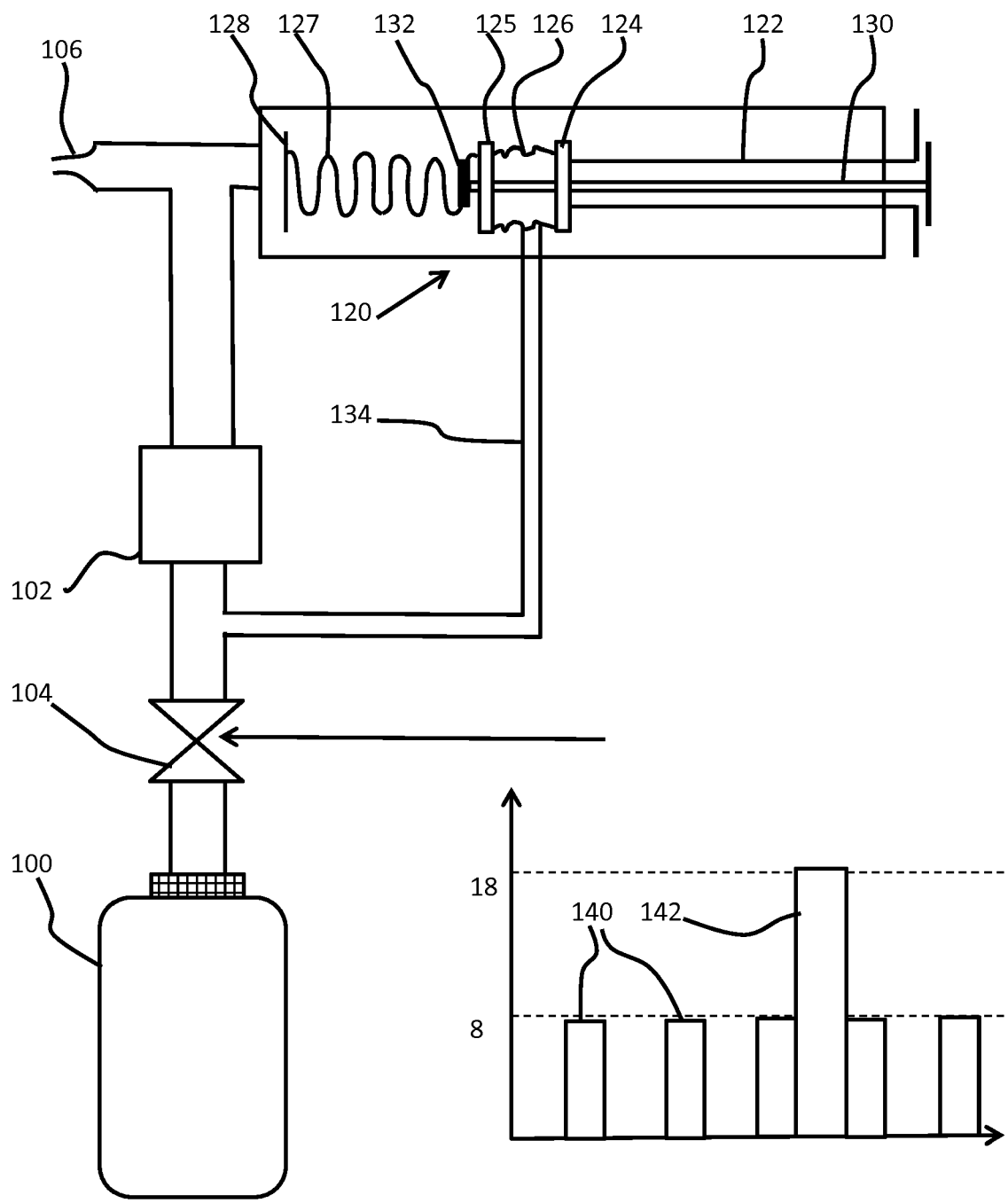
FIG. 9 shows a second example of pressure control system.
FIG. 10 shows a pressure time graph for the device of FIG. 9.

FIG. 9 shows a mechanical implementation. Passive resistive PEP valves are known, with the characteristic that the counter pressure imposed on the patient is substantially independent of the flow rate of exhaling. This is achieved by loading a spring to a set level, such that the flow is hampered below this pressure and easily flows above this pressure. Passive inspiratory muscle trainer (IMT) valves are also known, which impose a negative pressure upon inhaling.

FIG. 9 shows a system design which again enables a higher pressure to be provided upon inhalation by using a pneumatic rather than electronic design, making use of the pressure from the pressurized gas canister 100. This avoids using electronics and also eliminates the need for a separate pressure sensor, and may also be more fail safe.

FIG. 9 shows the same canister 100, user controlled valve 104 (which may again be automated) and pressure reducer 102. The user controlled valve is on the gas canister side of the pressure reducer 102 in this design.

The main valve part 120 has a first screw 122 which sets the location of a first plate 124. There is a second plate 125 with a bellows arrangement 126 between them. A spring 127 rests against the second plate 125 and the other end of the spring 127 is biased against an air valve 128.

The first screw 122 and first plate 124 set the positive PEP pressure. The first screw 122 is hollow and a second screw 130 runs through it, at the end of which there is a stop 132. By turning the second screw 130 relative to the first screw 122 the difference between the inspiratory Pressure and the expiratory pressure is set. Between the first plate 124 and the stop 132 there is a bellows, resting on the first plate and ending in the second plate 125, which can slide over the second screw. The bellows is connected to a pressure communication line 134 by means of a flexible tube. If the pressure is high, the second plate 125 rests on the stop 132. If there is no pressure, the second plate 125 rests close to the first plate 124.

When the second plate 125 is biased towards the stop 132, the valve 128 is more tightly closed. This happens when the user controlled valve is closed. When the second plate 125 is biased towards the first plate 124, the valve is partially open. This happens when the user controlled valve is open and it provides an increased positive pressure for an inhalation. With the lever closed, the valve maintains a lower internal pressure (generated by the patient) with the bellows forming a pressure feedback path.

By placing the pressure reducer 102 downstream of the user operated valve, the higher pressure is available for switching to the higher inspiratory pressure, which requires the work/power for compressing the spring quickly.

A small deliberate leak may be designed between the pressure reducer 102 and the mouthpiece 106, both to relieve the high pressure and thus allow the spring to return to its expanded shape for the expiratory pressure and to help the patient to attain the required expiratory pressure, as this gives a small concurrent gas flow.

This can alternatively be achieved by having the lever which the patient presses act as a valve, which is open to the mouthpiece if the patient is not pressing the lever, and closed if the level is pressed. This prevents air leakage from the high pressure reservoir during inhalation if this is unwanted.

There are alternative designs. For example, there may be two springs pressing against an air valve. The first spring may set the PEP pressure, the other spring loaded (or not) by a bellows attached to the end wall of the housing of the PEP/PIP valve. The bellows 126 may be replaced by a piston and cylinder, which has pressure-dependent position.

In this design, the pressure feedback path is mechanical and generally comprises a biasing element 126 which is controlled by the pressure at the outlet of the first user operated valve 104, and biases the second valve 128 towards a closed position. The bias of the second valve to the closed position with and without the bias of the biasing element is adjustable mechanically by the two screw adjusters 130, 132.

A typical pressure-time plot is shown in FIG. 10. The small peaks 140 are exhale pressure spikes, and the large peak 142 is when the patient applies the lever while inhaling.

The pressure reducer may take the form of an injector (making use of the Venturi effect), or it may be a fan driven by a turbine which itself is powered by the pressurized gas. This is also a purely pneumatic solution, avoiding a ventilator driven by an electrical motor. This is advantageous, as the pressure ratio of the compressed gas relative to the pressure in the mouthpiece is so high.

There are alternative mechanical implementations.

For example, a first valve is the user-operated valve.

A second valve is biased in one way only to deliver 8 cm $H_2O$ (=785 Pa) counter pressure when the first valve is closed.

A third valve is in parallel with the second valve. It is set at a higher pressure, such as 18 cm $H_2O$ (=1770 Pa), to set the inspiratory pressure. The third valve needs no further biasing relative to the first valve.

The third valve always opens at the given pressure. This then only requires only biasing of the second valve to open at e.g. 8 cm $H_2O$ (=785 Pa), or remain closed. Thus, a set of three more simple valves may be used to replace the two valves of FIG. 9 in which one in more complex as a result of the bidirectional biasing configuration.

The systems above enable at least PEP (Positive Expiratory Pressure), and in more extended exampled also Positive inspiratory Pressure (PIP) during a number of inhalations. The system is intended for small canisters which are bought pre-filled with their compressed gas, being air, enriched air or pure oxygen, depending on the type of patient and/or progression of their disease.

It is desirable that the patient can recharge these cans at home if their use is too heavy to be bought in large numbers, e.g. more than a few per week.

Existing oxygen sources and compressors are of a large capacity (of the order of one or several liters/second), bulky, and so expensive that patients can have such a device only on prescription with reimbursement.

It is also desirable that patients can buy an air compressing station only, which may suffice in the early stage of their disease (ventilation only), and later buy an oxygen source, if additional oxygen is needed to recover from a crisis, and have a feeling of comfort to have it with them to prevent anxiety.

A COPD patient in the early stage of the disease needs oxygen or compressed air at a flow rate of the order of a liter per second for a few seconds to minutes only. This flow rate and total volume can be delivered from a small canister of compressed gas, preferably mixed with ambient air. Such canisters may be bought if one uses only a few of them during a few crises per week. Upon heavier use, it is desirable to be able to recharge these cans at home, e.g. during the night.

Figures 11, 12:
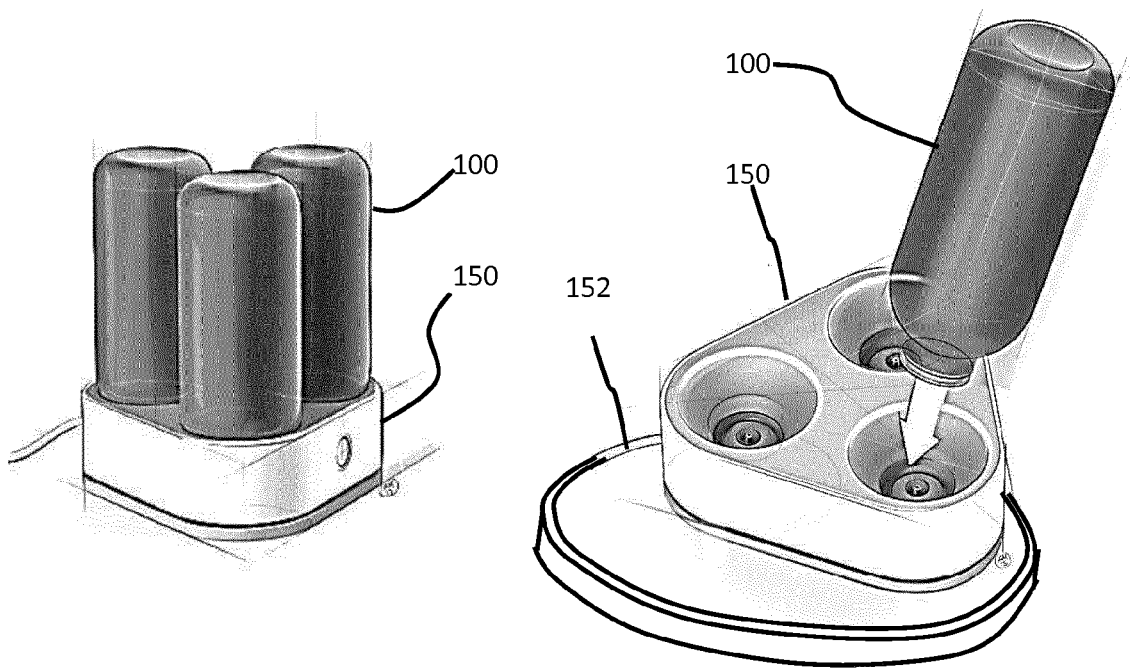
FIG. 11 shows three canisters being recharge in a docking station.
FIG. 12 shows how a canister is plugged into the docking station.

FIG. 11 shows three canisters 100 loaded into a recharging station 150 for recharging compressed air only or oxygen or oxygen enriched air. Thus, the charger is similar to that shown in FIG. 4 but is able to recharge multiple canisters. The charger 150 contains a small compressor for delivering pressurized gas at about 10 atm (1013250 Pa). The gas can be air, taken in through a slit running around the charger for ease of production, through a filter.

For linking the charger to the bottles, a screw connection may be used, for example a quarter turn connection, to allow a certain pressure to be maintained between the metal canister 100 and a rubber gasket ring, combined with a bayonet-type end lock to prevent unintended screwing-off As shown a number of bottles can be clamped into the charger to receive the compressed gas. Instead of loading the bottles in to the charger, the device with its connected canister may be loaded into the charger.

Of course three is only an example. A small oxygen concentrator may be provided which connects to the charger 150, as shown schematically as 152 in FIG. 12. This oxygen concentrator does not need its own power supply, as power can be taken by a plug from the charger. It does not have to contain a filter, as it can receive filtered air from the charger through a communication line.

It also does not have to contain its own air compressor, as the 10 atm (1013250 Pa) output pressure of the small compressor is more than enough to drive a pressure swing adsorption (PSA) oxygen concentration cycle. It delivers oxygen enriched gas to the charger through another communication line. Through a slit around the oxygen concentrator excess nitrogen is expelled.

At a flow rate of 30 ml/min, it takes 66 minutes to fill a 2 liter canister with gas to 10 bar. Three bottles can be charged in 200 minutes, about three and a half hours. There is then spare capacity to charge another batch of bottles, to charge larger bottles (e.g. 0.6 liters), or have a more limited charging power of only 10 ml/min, taking about 10 hours to completely fill three bottles of 0.2 liters.

The gas (and electrical if needed) communication lines between the two modules 150, 152 can be integrated in the form of a hollow metal tube. Integration of the gas compressor module and the oxygen concentrator module into one monolithic bloc is also possible.

The charger may be for receiving one or more gas canisters as shown, but it may also include one or more ports for receiving a complete device so that the user does not need to remove the gas canister to be able to replenish it.

The patient may then charge the gas canister, the battery attached to the gas canister, but also a fixed battery 154 (shown in FIG. 12 as a dark circle) of the device overnight by plugging in the entire device, with the gas canister remaining in it, into one of the ports of the charger.

The fixed battery 154 of the device for example enables the device to be used for monitoring breathing without needing a gas canister to be in place. The device thus comprises a second, rechargeable, battery 156 (also shown in FIG. 12 as a dark circle) within the housing. The battery of the portable gas canister may be used to recharge the second battery if the only the gas canister and its attached battery is plugged into the charger. If the whole device is plugged in, the second battery may be directly charged. When the device is used, the power may be preferentially drawn from the gas canister battery.

The fluidic port of the canister can for example be accessible through a hole in the housing of the device, and the electrical charging may be inductively through the plastic housing of the device.

The charging station may have a modular design, with an oxygen module which can later be bought and attached. The oxygen concentrator unit may have a simple click-on connection, not requiring its own internal or external power supply, nor its own compressor. Thus, the oxygen concentrator module of the charging station may be electrically powered by the docking station and operate a pressure swing adsorption oxygen concentration cycle using the pressure of the gas delivery path.

Figure 13:
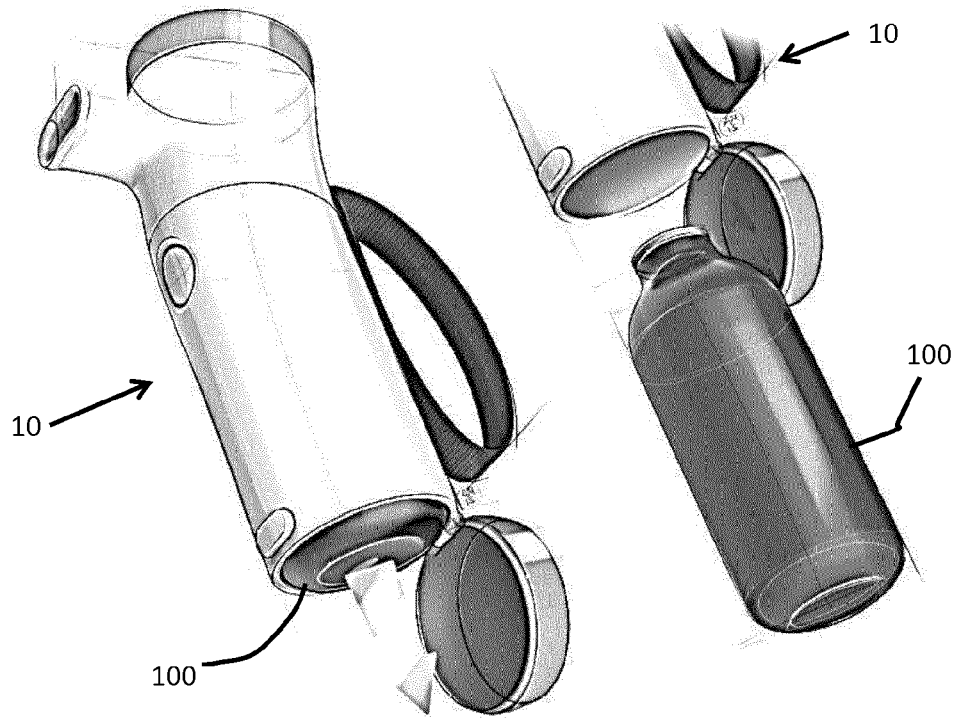
FIG. 13 shows how a canister is replaced in the portable device.

FIG. 13 shows the emptying of a spent canister 100 from the device and the loading of a new one.

Measures may be taken to prevent misuse of the supplied cans, or preventing use of the wrong canister in the device: This could take the form of a physical addition to the canister which is keyed to the charger 150. This key could encode information relating to the type of can, either pressurized, enriched or almost pure oxygen. This keying would prevent a copy or low quality replacement canister being used for safety reasons. It could also contain a shelf life to prevent the canister being over used.

The key could take the form of a printed image on the can; this can be read by a small optical reader as the canister is inserted. Of course, barcodes, QR codes may instead be used. An optical reader can be very basic if it only has to recognize one pattern. The key could also take the form of an RFID style reader with each canister having an RFID sticker; this would allow prescription or patient information to be embedded and then also prevent sharing of canisters when it would not be appropriate such as in the case of additional oxygen or future specific therapy types such as the inclusion of RDD (respiratory drug delivery) modules. The key could be purely mechanical.

As will be clear from the description above, the breathing assistance device in at least some examples includes electronic circuits, which require battery power, requiring loading of a battery into the device, or putting the devices onto a charging unit with regular checking of the remaining power level.

One option to ensure that the patient always has sufficient electrical energy available for the device, without having to worry about it, nor even know about the details will now be described. This aspect is based on providing the gas canister with a battery mounted into or onto it. The battery and the gas canister thus form a single module and the two parts are not separated by the user. In the case of a rechargeable battery, it may be charged electrically at the charging station as well so that with a recharged battery is plugged into the therapeutic device.

Thus, a gas supply system is provided for a portable breathing or assistance device, comprising a gas canister and a battery connected to the gas canister for providing power to the remainder of the device. If a rechargeable battery is used, then the gas canister and the rechargeable battery are adapted to be recharged from a common docking station. A docking station for the gas supply system for a portable breathing or assistance device then comprises a socket for receiving a gas canister, wherein the docking station comprises a gas delivery path to the canister and an electrical connection for providing electrical connection to a battery of the gas supply system.

The electrical power is available for the sensors and electronics, and also for powering a fan if such is used for mixing the ambient air with the decompressed gas.

If the canister is bought for one-time use (so that no charging function is needed), battery will be for one time use. In this case, there is an electrical connection between the canister and the rest of the device.

If the canister is to be replenished, a rechargeable battery may then be used. The weight may only be of the order of grams or tens of grams. This is sufficient to deliver enough electrical energy (a few Watt-hours).

The charger 150 then not only contains a gas compressor and communication line for the gas to the gas canister(s), but also a battery charger with an electrical communication line to the gas canister plus battery. These can be integrated into one connection.

The canister will be made out of metal to reliably withstand the gas pressure and multiple charging. As this poses a safety and reliability problem with unwanted discharging should a short circuit occur, it is best to cover the canister with a non-conduction cover or coating. There should be only tiny electrodes, preferably buried in a hole in the non-conducting cover, available for contacting the battery by the charger and therapeutic device.

One way to integrate the communication lines is to provide a conducting tube through which the gas runs into the canister. The connection may be spring biased so that electrical contact is only established if this tube is pressed onto. The spring can be non-conducting, or rest on a non-conduction plate. Similarly, the bottom electrode can be contacted only if an elastic metal membrane is pressed against an electrode.

The battery in/on the canister may be charged and/or discharged inductively by using a coil outside the metal canister.

For ensuring that the device functions properly, a color coded light on the therapeutic device to may be used to signify that electrical power is connected, as well as sufficient gas pressure, in any combination. For ensuring proper functioning, the canister may have a low power indicator of its electrically charged state, e.g. a passive liquid crystal display, an indicator of sufficient gas pressure (e.g. a color coded mechanical manometer), or a light that should light up if a button is pressed.

The examples of device above which include a gas canister are generally for use in a crisis situation. Preferably, the user does not have to switch on the device to use it in this mode. The device may thus auto-power-on when it detects patient breathing. One option is to use sensors within the device by leaving them in a low power state, and when a certain threshold is achieved, the device switches into full power mode. Alternatively, a passive actuator may be used to turn on when the airflow through the handset begins. This self-actuation could also extend to a wireless connection to a paired device, to share data or auto-connect at the same time, avoiding additional actions from the patient each time.

Note that the term "portable" when describing the device means that the whole device is portable—rather than there being a portable part and remote fixed part.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:
1. A portable breathing assistance device, comprising:
    a housing which defines a mouthpiece;
    a portable source of pressurized gas at a pressurization level, for providing gas to the user at a pressure above atmospheric pressure;

a pressure reducer configured to provide a pressure below the pressurization level at least during exhalation to provide a positive end-expiratory pressure; and a pressure control system controllable to regulate different pressures during inhalation and exhalation;

wherein the pressure control system comprises a first valve between the source of pressurized gas and the mouthpiece, a second valve between the mouthpiece and a vent to ambient air and a pressure feedback path for controlling the second valve to regulate the pressure at the mouthpiece in dependence on whether the first valve is open or closed;

wherein the pressure control system is arranged such that pressurized gas is configured to flow from the portable source of pressurized gas through the pressure reducer and then through the first valve; and an injector disposed downstream from the first valve and configured to mix the gas from the portable source of pressurized gas with ambient air;

wherein the second valve further comprises:
a first plate;
a first screw attached to the first plate and extending out an outlet of the second valve, wherein the first plate and the first screw are configured to set the positive end-expiratory pressure;
a second plate;
a biasing element operatively connected with the second plate;
a bellows connecting the first plate with the second plate; and
a second screw connected to the second plate;
wherein the second plate and second screw are configured to set a difference between the positive end-expiratory pressure and a positive end-inspiratory pressure.

2. The device as claimed in claim 1, wherein the first valve comprises a manually operated user control.

3. The device as claimed in claim 1, wherein the portable source of pressurized gas includes an outlet leading directly into an inlet of the pressure reducer.

4. The device as claimed in claim 1, wherein the pressure feedback path is mechanical and comprises the biasing element which is controlled by the pressure at the outlet of the first valve and configured to bias the second valve towards a closed position, wherein the bias of the second valve to the closed position with the bias of the biasing element is adjustable mechanically.

5. A portable breathing assistance device, comprising:
a housing which defines a mouthpiece;
a portable source of pressurized gas at a pressurization level, for providing gas to the user at a pressure above atmospheric pressure;
a pressure reducer configured to provide a pressure below the pressurization level at least during exhalation to provide a positive end-expiratory pressure; and
a pressure control system controllable to regulate different pressures during inhalation and exhalation;
wherein the pressure control system comprises:
a first valve between the source of pressurized gas and the mouthpiece,
a second valve between the mouthpiece and a vent to ambient air, and
a pressure feedback path for controlling the second valve to regulate the pressure at the mouthpiece in dependence on whether the first valve is open or closed;
wherein the pressure control system is arranged such that pressurized gas is configured to flow from the portable source of pressurized gas through the first valve and then the pressure reducer, wherein the second valve further comprises;
a first plate;
a first screw attached to the first plate and extending out an outlet of the second valve, wherein the first plate and the first screw are configured to set the positive end-expiratory pressure;
a second plate;
a biasing element operatively connected with the second plate;
a bellows connecting the first plate with the second plate; and
a second screw connected to the second plate;
wherein the second plate and second screw are configured to set a difference between the positive end-expiratory pressure and a positive end-inspiratory pressure.

6. The device as claimed in claim 5, wherein the screw is hollow and the second screw is configured to run through the screw.

7. The device as claimed in claim 5, wherein the second valve further includes:
a stop plate;
wherein a first end of the biasing member is attached to the stop plate and a second opposing end of the biasing member is attached to the second plate.

* * * * *